(12) United States Patent
Hackenschmied et al.

(10) Patent No.: US 10,014,430 B2
(45) Date of Patent: Jul. 3, 2018

(54) X-RAY DIRECT CONVERSION DETECTOR WITH ADDITIONAL RADIATION ILLUMINATION

(71) Applicant: Siemens Aktiengesellschaft, Munich (DE)

(72) Inventors: Peter Hackenschmied, Nuremburg (DE); Edgar Göderer, Forchheim (DE); Christian Schröter, Bamberg (DE); Matthias Strassburg, Klagenfurt (AT); Stefan Wirth, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 591 days.

(21) Appl. No.: 14/411,542

(22) PCT Filed: Jul. 10, 2013

(86) PCT No.: PCT/EP2013/064524
§ 371 (c)(1),
(2) Date: Dec. 29, 2014

(87) PCT Pub. No.: WO2014/019821
PCT Pub. Date: Feb. 6, 2014

(65) Prior Publication Data
US 2015/0168569 A1 Jun. 18, 2015

(30) Foreign Application Priority Data
Jul. 31, 2012 (DE) .................. 10 2012 213 411

(51) Int. Cl.
*H01L 27/146* (2006.01)
*H01L 27/148* (2006.01)
(Continued)

(52) U.S. Cl.
CPC ........... *H01L 31/16* (2013.01); *G01N 23/046* (2013.01); *H01L 27/1464* (2013.01);
(Continued)

(58) Field of Classification Search
CPC .... A61B 6/00; A61B 6/02; A61B 6/03; A61B 6/032; A61B 6/42; A61B 6/4208;
(Continued)

(56) References Cited

U.S. PATENT DOCUMENTS 3,886,370 A * 5/1975 Schubert ............ G01R 31/2656
250/206
4,875,084 A * 10/1989 Tohyama .......... H01L 27/14649
257/436
(Continued)

FOREIGN PATENT DOCUMENTS

CN 102187462 A 9/2011
DE 102010015422 A1 10/2011
(Continued)

OTHER PUBLICATIONS

International Search Report PCT/ISA/210 for International Application No. PCT/EP2013/064524 dated Nov. 27, 2013.
(Continued)

*Primary Examiner* — Anastasia Midkiff
(74) *Attorney, Agent, or Firm* — Harness, Dickey & Pierce, P.L.C.

(57) ABSTRACT

A method is disclosed for detecting incident X-ray radiation by way of a direct-converting X-ray radiation detector. A semi-conductor material used for detection purposes is irradiated with additional radiation with an energy level of at least 1.6 eV in order to produce additional charge carriers. A direct-converting X-ray radiation detector is disclosed for detecting X-ray radiation, at least including a semi-conductor material used for X-ray detection and at least one
(Continued)

radiation source which irradiates the semi-conductor material with additional radiation, the radiation having an energy level of at least 1.6 eV. A CT system including an X-ray radiation detector is also disclosed.

22 Claims, 3 Drawing Sheets

(51) Int. Cl.
*H01L 31/16* (2006.01)
*H01L 31/12* (2006.01)
*H01L 31/09* (2006.01)
*H01L 31/08* (2006.01)
*H01L 31/14* (2006.01)
*G01N 23/046* (2018.01)
*A61B 6/00* (2006.01)
*G01T 1/24* (2006.01)

(52) U.S. Cl.
CPC .. *H01L 27/14601* (2013.01); *H01L 27/14625* (2013.01); *H01L 27/14806* (2013.01); *H01L 31/085* (2013.01); *H01L 31/09* (2013.01); *H01L 31/125* (2013.01); *H01L 31/14* (2013.01); *A61B 6/4208* (2013.01); *G01T 1/24* (2013.01); *G01T 1/244* (2013.01)

(58) Field of Classification Search
CPC .............. A61B 6/4233; A61B 2560/00; A61B 2560/02; A61B 2560/16; G01T 1/00; G01T 1/16; G01T 1/24; G01T 1/244; G01T 7/00; H01L 27/00; H01L 27/14; H01L 27/142; H01L 27/144; H01L 27/146; H01L 27/14601; H01L 27/14618; H01L 27/14625; H01L 27/1464; H01L 27/14676; H01L 27/148; H01L 27/14806; H01L 31/08; H01L 31/085; H01L 31/09; H01L 31/095; H01L 31/115; H01L 31/12; H01L 31/125; H01L 31/14; H01L 31/16; H04N 5/30; H04N 5/32; H04N 5/335; H04N 5/3355; H04N 5/369; H04N 2201/0079
See application file for complete search history.

(56) References Cited

U.S. PATENT DOCUMENTS

| 5,563,421 | A | 10/1996 | Cheung |
| 5,905,772 | A * | 5/1999 | Rutten ...................... G01T 1/24 348/E3.052 |
| 6,373,064 | B1 * | 4/2002 | Yao ................... H01L 27/14665 250/370.13 |
| 7,652,258 | B2 * | 1/2010 | Shahar ..................... G01T 1/24 250/370.01 |
| 7,944,012 | B2 * | 5/2011 | Turchetta .......... H01L 27/14601 257/431 |
| 2004/0079891 | A1 | 4/2004 | Sato et al. |
| 2006/0027757 | A1 | 2/2006 | Sato et al. |
| 2008/0164418 | A1 | 7/2008 | El-Hanany |
| 2009/0266992 | A1 | 10/2009 | Beekman |
| 2010/0119040 | A1 | 5/2010 | Suyama et al. |
| 2011/0200166 | A1 | 8/2011 | Hackenschmied et al. |
| 2011/0253886 | A1 | 10/2011 | Hackenschmied |

FOREIGN PATENT DOCUMENTS

| EP | 1394567 A2 | 3/2004 |
| EP | 1394567 A2 | 3/2004 |
| JP | 2010117172 A | 5/2010 |
| WO | WO 0068710 A2 | 11/2000 |

OTHER PUBLICATIONS

Written Opinion of the International Searching Authority PCT/ISA/237 for International Application No. PCT/EP2013/064524 dated Nov. 27, 2013.
Polarisationskompensierter Hochfluss-Strahlendetektor; Published on Jun. 25, 2009 (with Partial English translation).
Auf Ladungsträgerdiffusion basierter Hochfluss-Strahlendetektor; Published on May 28, 2009 (with Partial English translation).
Chinese Office Action and English translation thereof dated Apr. 20, 2016.

* cited by examiner

FIG 1

X-RAY DIRECT CONVERSION DETECTOR WITH ADDITIONAL RADIATION ILLUMINATION

PRIORITY STATEMENT

This application is the national phase under 35 U.S.C. § 371 of PCT International Application No. PCT/EP2013/064524 which has an International filing date of Jul. 10, 2013, which designated the United States of America, and which claims priority to German patent application DE 102012213411.5 filed Jul. 31, 2012, the entire contents of each of which are hereby incorporated herein by reference.

FIELD

At least one embodiment of the invention generally relates to a method for detecting incident X-ray radiation by way of a direct-converting X-ray radiation detector. At least one embodiment of the invention also generally relates to a direct-converting X-ray radiation detector for detecting X-ray radiation, at least having a semiconductor material used for detecting X-ray radiation and at least one radiation source which irradiates the semiconductor material with additional radiation, and to a CT system having an X-ray radiation detector.

BACKGROUND

For the detection of gamma and X-ray radiation in particular in CT, SPECT and PET systems, inter alia direct-converting detectors are used, or their use is intended, which are based on semiconducting materials such as CdTe, CdZnTe, CdZnTeSe, CdTeSe, CdMnTe, InP, TlBr2, HgI2. However the effect of polarization occurs with these materials, in particular with a high radiation flux density that is necessary for CT devices.

Polarization refers to the reduction in the detected count rate with high photon fluxes or radiation fluxes. This polarization is caused by the very low mobility of charge carriers, predominantly of electron vacancies or holes, and by the concentration of intrinsic vacancies in the semiconductor. In other words, polarization occurs as a result of the reduced electric field caused by stationary charges bound to vacancies, which function as absorption and recombination centers for the charge carriers generated by the radiation. This results in a reduced charge carrier lifetime and mobility, which in turn leads to a reduction in the detected count rate with high photon fluxes.

However a radiation detector has to have a high charge carrier lifetime and mobility so that the electrons and holes that occur during irradiation can be separated. The maximum detectable radiation flux of a direct converter is otherwise limited as a result of polarization. For this reason it has hitherto not been possible to convert high radiation densities, such as those predominantly employed in computed tomography, directly and without loss into electrical pulses.

The publication US 2008/0164418 A1 describes a method for reducing polarization in a semiconductor detector, in which electrical signals are generated in response to the absorption of an ionizing radiation in the semiconductor, wherein a space charge occurs in the semiconductor and, as a function of the space charge generated, the semiconductor is irradiated with one or more wavelengths of IR radiation so as to at least partially reduce the polarization in the semiconductor and thus its effect on the electrical signals. The IR radiation used has a maximum energy of 1.57 eV with a wavelength of at least 790 nm.

SUMMARY

At least one embodiment of the invention provides an improved method for the detection of X-ray radiation in a direct-converting X-ray radiation detector, wherein the polarization in a semiconductor material used for detection purposes is prevented almost entirely.

Advantageous developments of the invention are the subject matter of subordinate claims.

The inventors accordingly propose, in at least one embodiment, a method for detecting incident X-ray radiation by way of a direct-converting X-ray radiation detector, in particular for use in a CT system, wherein a semiconductor material used for detection purposes is irradiated with additional radiation with an energy of at least 1.6 eV, in order to generate additional charge carriers. With a method of this kind the polarization in the semiconductor is prevented by the semiconductor being irradiated with high-energy radiation in addition to the X-ray radiation to be detected. However this additional radiation is not detected and is not used for imaging purposes. It serves purely to generate additional charge carriers. In accordance with the invention, radiation with an energy of at least 1.6 eV is used for this purpose. This corresponds to a maximum wavelength of 770 nm. In a preferred embodiment radiation with an even higher energy, in other words preferably more than 2.1 eV, further preferably between 2.1 eV and 3.2 eV, is used.

At least one embodiment of the invention also relates to a direct-converting X-ray radiation detector for detecting X-ray radiation in accordance with the method described above, in particular for use in a CT system, at least having a semiconductor material for the detection of X-ray radiation and at least one radiation source that irradiates the semiconductor material with an additional radiation, wherein the radiation has an energy of at least 1.6 eV. Semiconductor materials such as CdTe, CdZnTe, CdZnTeSe, CdTeSe, CdMnTe, InP, TlBr2, HgI2 are suitable for detection purposes. The radiation used is advantageously electromagnetic radiation in the visible range and/or UV range or electron beam radiation. Accordingly for example at least one electromagnetic radiation source, in particular a light-emitting diode, and/or at least one electron beam radiation source, is used as the radiation source. In one embodiment precisely one radiation source is embodied that irradiates the semiconductor material. In other embodiments a plurality of radiation sources are provided that irradiate the semiconductor material for example also from differing directions and/or with differing energies, in order to ensure that an irradiation is as even as possible and thus that charge carriers are generated evenly in the semiconductor material. In accordance with the invention the radiation source generates high-energy radiation with at least 1.6 eV, preferably more than 2.1 eV.

Also included within the scope of at least one embodiment of the invention is a CT system, comprising an X-ray radiation detector with an additional radiation source, with which tomographic images of an examination object can be produced in accordance with at least one embodiment of the method described above.

BRIEF DESCRIPTION OF THE DRAWINGS

The invention is described in more detail below on the basis of preferred example embodiments with the aid of the figures, wherein only the features required to understand the invention are shown. The following reference signs are used: A: anode; C1: CT system; C2: first X-ray tube; C3: first detector; C4: second X-ray tube (optional); C5: second detector (optional); C6: gantry housing; C7: patient; C8: patient couch; C9: system axis; C10: computing and control unit; HL: semiconductor; K: cathode, Prg1 to Prgn: computer programs; Q: radiation source; S: coating.

In the figures.

DETAILED DESCRIPTION OF THE EXAMPLE EMBODIMENTS

The inventors have recognized that polarization in the semiconductor material used for detection purposes can be prevented through the generation of an additional space charge or additional charge carriers in the semiconductor material. These additionally-generated charge carriers can fill and thus passivate the intrinsic vacancies in the semiconductor crystal, in particular the deep vacancies. Stationary charges therefore occur that prevent the formation of a space charge and thereby the polarization of the semiconductor.

The charge carriers can be applied to the semiconductor material by way of high-energy radiation. The radiation used has a minimum energy of 1.6 eV. For this purpose electromagnetic radiation, such as visible light or ultraviolet radiation, or electron beam radiation, can be used for example. For comparison purposes, the IR radiation used in the publication US 2008/0164418 A1 cited above has a maximum energy of merely 1.57 eV with a wavelength of at least 790 nm. The semiconductor material is then irradiated with a pulse or continuously, during and/or at a defined time interval before the X-ray radiation and/or with differing or identical energies.

The charge carriers are generated close to the surface of the semiconductor material as a result of the irradiation and diffuse or drift from there into the interior of the semiconductor material. Various possibilities exist for directing the irradiation, for example to the cathode side and/or anode side, for example by way of semitransparent contacts on a surface of the semiconductor or by way of gaps in an electrode mask of the detector or from the side. In the case of use in a CT system, the radiation source can be disposed on the z side on the semiconductor so that the semiconductor is irradiated from a z direction.

The selection of the energy or wavelength for radiation in the visible range is based on the bandgap of the particular semiconductor material being used. If the energy of the light radiation is greater than the energy difference of the bandgap, band-to-band excitation of the charge carriers occurs. In other words, band-to-band transitions of the charge carrier are possible. For example, CdTe has a bandgap of 1.4 eV at room temperature. This corresponds to a wavelength of around 850 nm, in other words near-IR radiation. Therefore, to enable band-to-band transitions in CdTe, radiation with a shorter wavelength and thus greater energy, i.e. with more than 1.6 eV, is used. However with increasing energy or decreasing wavelength of the light radiation, the penetration depth of the light radiation into the semiconductor material reduces so that the absorption of the light radiation occurs increasingly in a potentially disordered surface layer of the semiconductor. The charge carrier generation can then become inefficient. Consequently with the use of visible light radiation it is expedient for the radiation energy to be matched to the energy of the bandgap and not to deviate from the energy of the bandgap by more than 25% for example.

Another possibility for applying additional charge carriers in the semiconductor is to generate the visible radiation on evaluation electronics of the CT system, the ASIC (application-specific integrated circuit), and to feed the visible radiation into the semiconductor by way of a translucent contact material. For this purpose a radiation source can be directly grown on, deposited on and/or mechanically connected to the ASIC. The radiation source can be for example light-emitting diodes (LEDs). These radiation sources can be disposed below each inter-pixel gap or at the edge of the ASIC. Such an embodiment of the radiation source also enables anode-side or cathode-side irradiation of the semiconductor.

Essentially, by irradiating the cathode, the charge carriers, in other words negative electrons and positive holes, are formed a few micrometers below the cathode in the semiconductor. The holes recombine directly at the cathode, while the electrons pass through the semiconductor material and thus also fill vacancies in the interior of the semiconductor. A positive space charge occurs. With anode-side irradiation, precisely the opposite happens. The holes pass through the semiconductor material and also fill vacancies in the interior of the semiconductor, so that a negative space charge occurs. The formation of the space charge in the semiconductor material, and thus the polarization state, can be influenced or controlled by means of a cathode-side and/or anode-side irradiation of the semiconductor. The proportions of anode-side or cathode-side irradiation are selected so that the resulting space charge corresponds to the opposite space charge occurring under X-ray irradiation. For example a negative space charge caused by X-ray radiation is compensated for by a positive space charge caused by the additional charge carriers generated. The space charge therefore still also remains constant with incident X-ray radiation in the semiconductor material. Consequently the detector response is stabilized.

With a simultaneous and/or sequential anode-side and/or cathode-side irradiation, in particular a combination of differing wavelength ranges or energy ranges and differing intensities can be selected. For example an energy range and the intensity of radiation is varied as a function of kV and mAs settings of a planned X-ray scan in a CT system, in order optimally to match the space charge to the profile of the energy deposition within the X-ray radiation detector.

Essentially the previously relevant vacancies in the semiconductor, at which the space charge is formed and which lead to polarization, are passivated or compensated for, so that the semiconductor material is suitable as a direct-converting X-ray radiation detector for high-flux operation, for example in CT systems or dual-energy CT systems.

The inventors accordingly propose, in at least one embodiment, a method for detecting incident X-ray radiation by way of a direct-converting X-ray radiation detector, in particular for use in a CT system, wherein a semiconductor material used for detection purposes is irradiated with additional radiation with an energy of at least 1.6 eV, in order to generate additional charge carriers. With a method of this kind the polarization in the semiconductor is prevented by the semiconductor being irradiated with high-energy radiation in addition to the X-ray radiation to be detected. However this additional radiation is not detected and is not used for imaging purposes. It serves purely to generate additional charge carriers. In accordance with the invention, radiation with an energy of at least 1.6 eV is used for this purpose. This corresponds to a maximum wavelength of 770 nm. In a preferred embodiment radiation with an even higher energy, in other words preferably more than 2.1 eV, further preferably between 2.1 eV and 3.2 eV, is used.

Additional charge carriers, in other words electrons and holes, are generated in the semiconductor by means of the high-energy radiation. The charge carriers generated in this way fill the vacancies, in particular the deep vacancies, in the semiconductor material, which are consequently neutralized and stationary charges occur. This prevents the formation of a space charge at the vacancies and thus prevents polarization. A high charge carrier lifetime and mobility is advantageously thus maintained so that even with high photon fluxes the detected count rate is not reduced. Consequently the maximum detectable radiation flux of the direct-converting X-ray radiation detector is not limited by polarization. In accordance with the invention, high radiation densities, preferably in CT systems, can also be converted directly into electrical pulses.

Differing radiation, in particular differing high-energy radiation, can be used for irradiation of the semiconductor, and can be radiated onto the semiconductor material from different directions simultaneously and/or at different times. In one embodiment, electromagnetic radiation is used, preferably visible light and/or ultraviolet radiation. The energy of the visible radiation ranges from approx. 1.6 eV with a wavelength of approx. 770 nm up to an energy of approx. 3.1 eV with a wavelength of approx. 400 nm. The energy range of ultraviolet radiation lies between approx. 3.3 eV and approx. 12 eV with a wavelength of approx. 380 nm to 1 nm. Preferred energy range of the radiation is determined based on the radiation source used and the radiation's intended penetration depth into the semiconductor material, for example the energy of the radiation with an AlGaN LED is approx. 3.5 eV. With the use of visible light radiation, the advantageous energy of the radiation is in each case a function of the energy of the bandgap of the semiconductor material of the X-ray radiation detector. Advantageously the energy of the radiation is no more than 25% greater than the energy difference of the bandgap, as otherwise the penetration depth of the light radiation into the semiconductor material is too low and too few charge carriers are generated.

In another embodiment the semiconductor material is irradiated with electron beam radiation. The energy of the electron beam radiation used lies between approx. 1 eV and 10 keV. If electron beam radiation is used for the generation of charge carriers, the penetration depth increases with the energy of the radiation so that, with high-energy X-ray radiation, the charge carriers are generated increasingly in the interior of the semiconductor material.

The radiation type used and its energy or dose are determined based on the intended penetration depth of this radiation into the semiconductor material and based on the position of the defects in the semiconductor material that are intended to be passivated by the additionally-generated charge carriers. If the defects are near the surface, radiation with a lower penetration depth can be used.

Depending on the embodiment, the semiconductor material is irradiated on the anode side and/or on the cathode side. In one embodiment the irradiation is performed on the anode side with a radiation source disposed on the side of the anode. In another embodiment the irradiation is performed on the cathode side with a radiation source disposed on the side of the cathode. In this embodiment it is furthermore possible to switch back and forth between the anode-side and cathode-side irradiation, for example sequentially, so that the irradiation is performed alternately on the anode side or on the cathode side. Another embodiment provides for simultaneous irradiation on the anode side and on the cathode side. In this case differing wavelength ranges or energy ranges of the radiation additionally can be combined with each other, for example high-energy radiation on the cathode side can be used for the generation of charge carriers close to the contact, so that the holes, despite their low mobility, can be collected by the cathode and the electrons can travel through the whole of the semiconductor crystal. Simultaneously in the interior of the semiconductor crystal a constant defect level and thus a constant internal electric field can occur as a result of the irradiation from the anode side with low-energy radiation, which penetrates more deeply into the semiconductor crystal. Here the radiation source is disposed either between the anode or cathode and the semiconductor material, or on an outer side of the anode or cathode. In this case the anode or cathode is preferably at least partially translucent, for example as a grid structure or based on the material selected for the anode or cathode.

For example an anode-side or cathode-side irradiation can also be performed by way of gaps in an electrode mask of the X-ray radiation detector and/or by way of evaluation electronics. In one embodiment, the electrodes are so thinly deposited for this purpose that firstly the penetration depth of the radiation is greater than the coating thickness of the electrode and/or the electrode does not constitute a complete and uniform coating or constitutes a coating with thickness variations. For example, visible light radiation penetrates a 10 to 50 nm thick gold or platinum electrode so that charge carrier pairs are generated in the semiconductor.

With anode-side or cathode-side irradiation with visible light, the charge carriers occur in each case directly at the anode or cathode in the semiconductor. If the cathode is irradiated, the holes generated recombine directly without penetrating more deeply into the semiconductor material, while the electrons diffuse into the interior of the semiconductor and fill the vacancies there. However if the anode is irradiated, by contrast the holes diffuse into the semiconductor material and fill the vacancies, while the electrons recombine directly with the anode. Thus the space charge formed is distinguished by the direction of irradiation. Depending on the type of space charge, the polarization state is influenced in the semiconductor. The polarization state in the semiconductor caused by X-ray radiation is advantageously the opposite of the polarization state formed by way of the additionally-generated charge carriers, so that the two polarization states cancel each other out. In accordance with the invention a positive polarization state caused by X-ray radiation is compensated for by a negative polarization state resulting from the additional irradiation, and vice versa.

Figure 5:
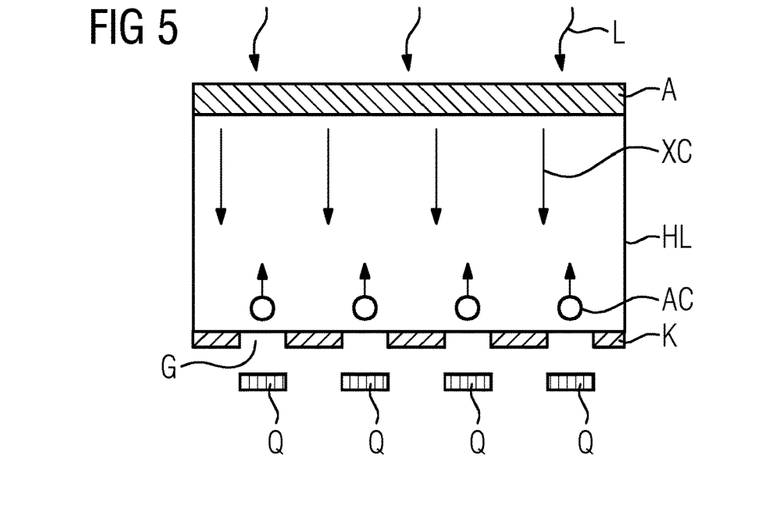
FIG. 5 shows a schematic representation of a semiconductor with a cathode-side radiation source.
Figure 6:
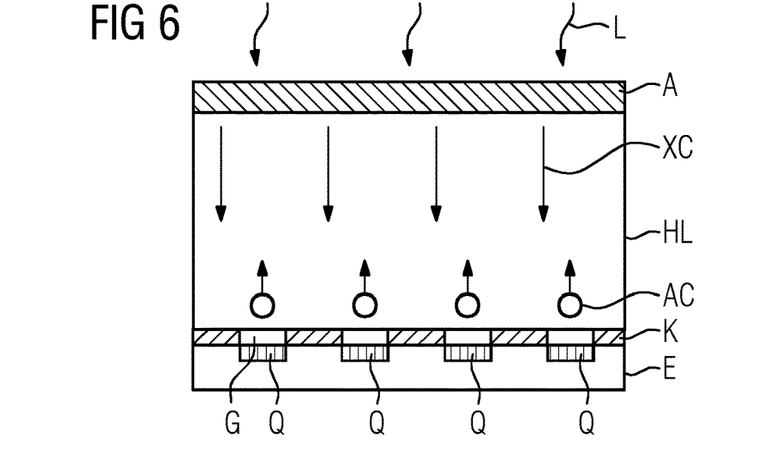
FIG. 6 shows a schematic representation of a semiconductor with a cathode-side radiation source.

An anode-side or cathode-side irradiation is performed in other embodiments by way of gaps G (FIGS. 5 and 6) in an electrode mask of the X-ray radiation detector and/or by way of evaluation electronics E (FIG. 6). In one embodiment, visible radiation is fed into the semiconductor by way of the evaluation electronics E of the CT system. This takes place advantageously by way of a translucent contact material. One or a plurality of LEDs are particularly suitable for use as a radiation source. The LEDs can be directly grown on, deposited on and/or mechanically connected to the evaluation electronics E. Advantageously the LEDs are disposed below each inter-pixel gap and/or at the edge of the evaluation electronics E. This enables both a cathode-side and an anode-side irradiation of the semiconductor. Furthermore this embodiment is advantageously space-saving as no additional and separate radiation sources are used.

In one embodiment the irradiation is performed on both the anode side and cathode side. Advantageously in this case a signal transmission by means of electrons and holes is supported by the additional charge carriers.

Alternatively and/or in addition to the anode-side or cathode-side irradiation, the semiconductor is irradiated from the side and/or by way of semitransparent contacts. The radiation source is then disposed either directly on or at a distance from the semiconductor material. With the use of electron beam radiation a cathode-side irradiation is advantageous if a signal transmission by means of electrons is performed. Since the charge carriers generated must in all cases pass through the whole of the component toward the anode, the desired effect is achieved even with illumination that is uneven in terms of intensity or that has low penetration depth. By contrast, an anode-side irradiation with X-ray radiation is advantageous if a signal transmission by means of the positive holes is performed.

In a further embodiment, in particular with a use of at least one embodiment of the inventive method in a CT system, the semiconductor material is preferably irradiated from a z direction and/or a circumferential direction C11 of the CT system.

In addition, as well as the type of radiation, its direction of incidence and/or the radiation energy, it is also possible to vary a duration of irradiation and/or a time of irradiation. For example the semiconductor material can be irradiated with a pulse and/or continuously. The duration of the irradiation or of the individual pulses is determined based on the number of defects needing to be passivated. A longer irradiation is advantageous with a large number. Furthermore a pulsed irradiation advantageously achieves a quasi-stationary state in the semiconductor material. The duration and interval of the pulses are determined furthermore based on the lifetime of the defect complexes following irradiation.

The irradiation can be performed before and/or during the incidence of the X-ray radiation to be detected. A time interval between the additional irradiation and the X-ray radiation is also determined based primarily on the lifetime of the defect complexes following the irradiation. If this is very high, for example several minutes, the irradiation can be performed with a longer interval, also for example several minutes. However, the time interval until the X-ray radiation is advantageously smaller than the lifetime of the defects mentioned above.

In addition the radiation energy can be changed during the irradiation, for example continuously or in steps. In this case the radiation energy is reduced, in other words changed in the direction of smaller energy values, in one embodiment. In another embodiment the radiation energy is increased, in other words changed in the direction of greater energy values. By changing the radiation energy, the compensation of the polarization state in the semiconductor can be matched advantageously to the energy flows of an X-ray scan.

By way of the irradiation of the semiconductor, band-to-band transitions are excited in the semiconductor material, in particular with the use of visible light radiation. Here the energy of the radiation is preferably greater than the energy of a bandgap of the particular semiconductor material, in order to excite the charge carriers sufficiently. However with visible light radiation the penetration depth of the radiation into the material decreases such that the charge carrier generation takes place almost entirely in a surface layer of the semiconductor material. However there may potentially be defects here, which makes the charge carrier generation inefficient. In order to avoid this problem, the radiation energy is advantageously matched to an energy difference of a band-to-band transition in the semiconductor material. The radiation energy preferably deviates by not more than 25%, preferably not more than 20%, further preferably not more than 15%, from the energy difference of the bandgap.

At least one embodiment of the invention also relates to a direct-converting X-ray radiation detector for detecting X-ray radiation in accordance with the method described above, in particular for use in a CT system, at least having a semiconductor material for the detection of X-ray radiation and at least one radiation source that irradiates the semiconductor material with an additional radiation, wherein the radiation has an energy of at least 1.6 eV. Semiconductor materials such as CdTe, CdZnTe, CdZnTeSe, CdTeSe, CdMnTe, InP, TIBr2, HgI2 are suitable for detection purposes. The radiation used is advantageously electromagnetic radiation in the visible range and/or UV range or electron beam radiation. Accordingly for example at least one electromagnetic radiation source, in particular a light-emitting diode, and/or at least one electron beam radiation source, is used as the radiation source. In one embodiment precisely one radiation source is embodied that irradiates the semiconductor material. In other embodiments a plurality of radiation sources are provided that irradiate the semiconductor material for example also from differing directions and/or with differing energies, in order to ensure that an irradiation is as even as possible and thus that charge carriers are generated evenly in the semiconductor material. In accordance with the invention the radiation source generates high-energy radiation with at least 1.6 eV, preferably more than 2.1 eV.

Also included within the scope of at least one embodiment of the invention is a CT system, comprising an X-ray radiation detector with an additional radiation source, with which tomographic images of an examination object can be produced in accordance with at least one embodiment of the method described above.

Overall at least one embodiment of the invention offers at least one of the following advantages:

By way of at least one embodiment of the inventive method, the polarization state of the detector can be controlled or influenced so that the polarization or drift of the detector under X-ray irradiation can be avoided. In particular the polarization state can be matched to the particular usage situation in the device. In this way image artifacts in imaging methods, such as computed tomography, angiography, single-photon emission computed tomography, positron emission tomography, etc. are in turn avoided. The inventive X-ray radiation detector offers a simple and above all space-saving structure through the use of compact and small components, for example the LEDs. The semiconductor materials used are easily and cheaply available, as they are industrially-produced materials. Furthermore the properties of the LEDs have been researched extensively and can therefore easily be matched to the desired energy range.

Such light sources can also be obtained cheaply. Furthermore the homogeneity of the individual channels or pixels of the detector can be improved.

Figure 1:
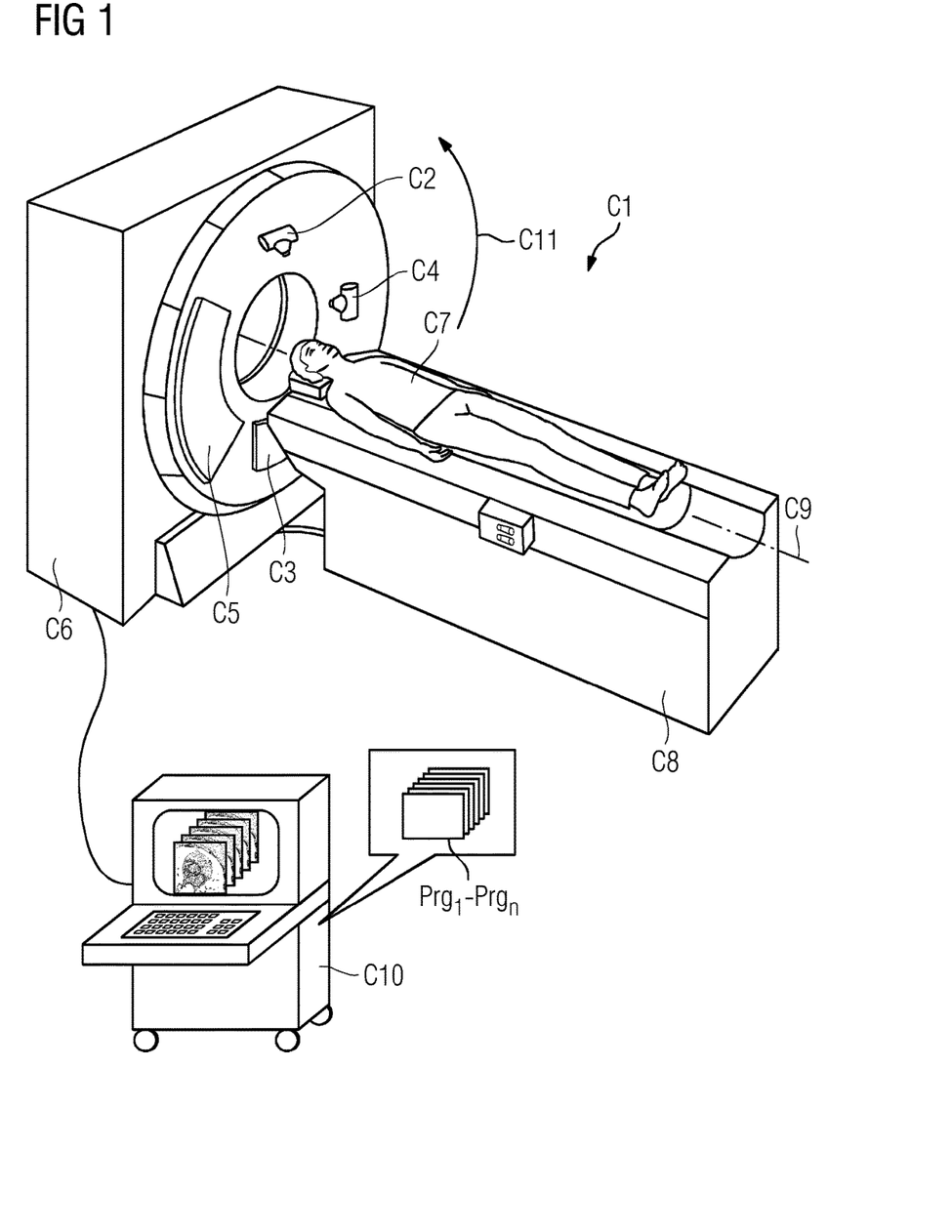
FIG. 1 shows a schematic representation of a CT system with computing unit.

FIG. 1 shows a CT system C1 by way of example. The CT system C1 comprises a gantry housing C6 in which is located a gantry (not shown in any further detail here), on which a first X-ray tube C2 with an opposing first detector C3 is affixed. Optionally a second X-ray tube C4 with a second opposing detector C5 is provided. A patient C7 is positioned on a patient couch C8 that is movable in the direction of the system axis C9, and during the scan with the X-ray radiation he can be moved, using said patient couch, continuously or sequentially along the system axis C9 in the z direction, through a measurement field between the X-ray tubes C2 and C4 and their respectively assigned detectors C3 and C5. This procedure is controlled by a computing and control unit C10 with the aid of computer programs Prg1 to Prgn.

Figure 2:
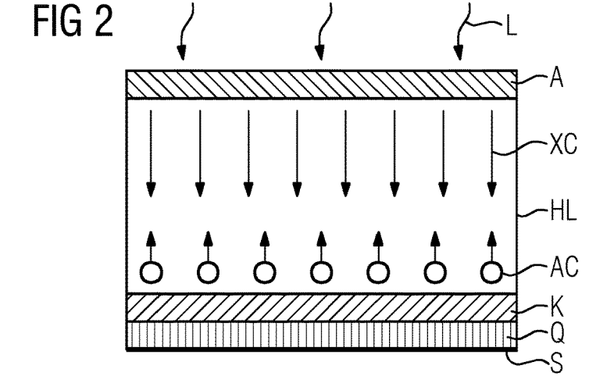
FIG. 2 shows a schematic representation of a semiconductor with a cathode-side radiation source in a first embodiment.
Figure 3:
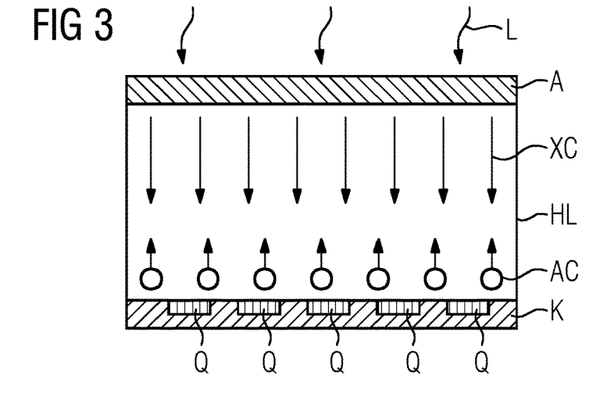
FIG. 3 shows a schematic representation of the semiconductor with the cathode-side radiation source in a further embodiment.
Figure 4:
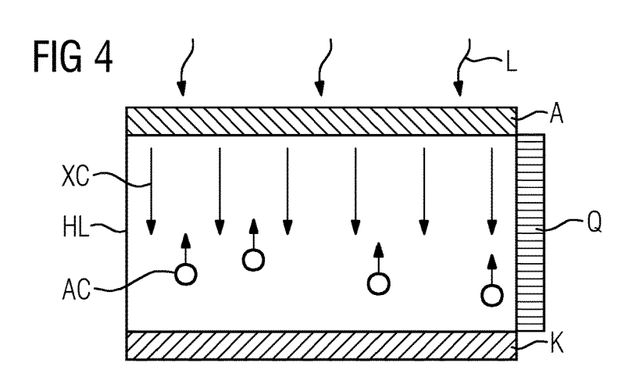
FIG. 4 shows a schematic representation of a semiconductor with a radiation source disposed laterally.

In accordance with an embodiment of the invention the detectors C3 and C5 are embodied as direct-converting X-ray radiation detectors having a semiconductor material used for detecting X-ray radiation and an additional radiation source for generating additional charge carriers in the semiconductor (see FIGS. 2 to 4). The CT system C1 is accordingly operated in accordance with an embodiment of the inventive method.

Each of the FIGS. 2 to 4 shows a schematic representation of a semiconductor material HL of a detector element, which is used for detecting X-ray radiation. The semiconductor material HL is CdTe for example. On two opposing sides of the semiconductor HL an anode A and a cathode K are disposed on the semiconductor HL. The anode A and the cathode K conventionally are connected to electronics of the CT system, which however for the sake of clarity are not shown here. In accordance with the invention each of FIGS. 2 to 4 show at least one radiation source Q. The radiation sources Q are embodied by way of example as LEDs for generating visible light radiation with an energy range of 1.6 eV to 3.2 eV. In accordance with the invention this results in an additional irradiation of the semiconductor HL being performed to generate additional charge carriers AC and thus to compensate for a polarization in the semiconductor HL caused by the incident X-ray radiation L which produces charge carriers XC. The embodiments shown in FIGS. 2 to 4 differ in each case in the arrangement and embodiment of the radiation sources Q.

FIG. 2 shows a cathode-side radiation source Q. The radiation source Q is embodied so as to be flat or layered and is disposed directly on the side of the cathode K opposite to the semiconductor HL. For this purpose the cathode K is embodied so as to be translucent. The light radiation emanating from the radiation source Q flows through the cathode K and penetrates the semiconductor material HL, where it generates additional charge carriers AC. For more targeted emission of the light radiation from the radiation source Q into the semiconductor material HL, a mirrored coating S is applied on the outer side of the cathode K that reflects the radiation to the semiconductor HL. By way of the flat embodiment of the radiation source Q, an even irradiation of the semiconductor HL and thus an even charge carrier generation are achieved. With the cathode-side arrangement of the radiation source Q, the holes generated recombine directly at the cathode K. The electrons generated diffuse into the interior of the semiconductor HL and fill the vacancies there. In accordance with the invention the positive space charge thus formed through the X-ray radiation to be detected can be compensated for by a negative space charge of the additional charge carriers AC. The polarization of the semiconductor HL is ultimately avoided.

FIG. 3 shows a further embodiment of radiation sources Q disposed on the cathode side. Here five individual radiation sources Q are introduced into gaps G (FIG. 5) in the cathode K, in other words between cathode K and semiconductor HL. In this embodiment the radiation is radiated directly into the semiconductor HL. By means of the even distribution of the radiation sources Q on the semiconductor HL, an even irradiation and generation of charge carriers is also achieved here.

The cathode-side arrangement of radiation sources Q shown in FIGS. 2 and 3 and its functionalities correspond analogously to an anode-side arrangement of the radiation source Q.

FIG. 4 shows a radiation source Q disposed laterally on the semiconductor HL. The radiation source Q is disposed directly on the semiconductor HL and is embodied so as to be flat, in order to ensure that an irradiation is as even as possible.

Although the invention has been illustrated and described in detail on the basis of the preferred example embodiment, the invention is not limited by the disclosed examples and other variations can be derived herefrom by the person skilled in the art, without departing from the scope of protection of the invention.

The invention claimed is:

1. A method for detecting incident X-ray radiation by way of a direct-converting X-ray radiation detector that generates charge carriers in a semiconductor material, the method comprising:
    irradiating the semiconductor material, used for detection purposes, with additional radiation with an energy of at least 1.6 eV and less than 10 keV, to generate additional charge carriers, wherein the semiconductor material is irradiated with the additional radiation by way of evaluation electronics.

2. The method of claim 1, wherein the semiconductor material is irradiated with the additional radiation with an energy greater than 2.1 eV.

3. The method of claim 1, wherein the semiconductor material is irradiated with electromagnetic radiation via the additional radiation.

4. The method of claim 1, wherein the semiconductor material is irradiated with electron beam radiation via the additional radiation.

5. The method of claim 1, wherein the semiconductor material is irradiated with the additional radiation on at least one of an anode side and a cathode side.

6. The method of claim 1, wherein the semiconductor material is irradiated with the additional radiation from at least one of a z direction and a circumferential direction of a rotary detector support of a computed tomography (CT) system.

7. The method of claim 1, wherein the semiconductor material is irradiated with the additional radiation with a pulse or continuously.

8. The method of claim 1, wherein the semiconductor material is irradiated with the additional radiation at least one of before and during the incidence of the X-ray radiation to be detected.

9. The method of claim 1, wherein the additional radiation comprises different energies and the semiconductor material is irradiated with the additional radiation with differing energies.

10. The method of claim 9, wherein the irradiating includes changing the energy of the additional radiation during the irradiation.

11. The method of claim 1, wherein the irradiating includes exciting band-to-band transitions in the semiconductor material during the irradiation.

12. The method of claim 11, wherein the energy of the additional radiation is no more than 25% greater than an energy difference of the band-to-band transitions.

13. A direct-converting X-ray radiation detector for detecting X-ray radiation, comprising:
- a semiconductor material used for detecting X-ray radiation;
- evaluation electronics; and
- at least one additional radiation source to irradiate the semiconductor material with additional radiation by way of the evaluation electronics, wherein the additional radiation has an energy of at least 1.6 eV and less than 10 keV.

14. The X-ray radiation detector of claim 13, wherein the at least one additional radiation source includes at least one of an electromagnetic radiation source and an electron beam radiation source.

15. A CT system comprising the X-ray radiation detector of claim 14.

16. The method of claim 1, wherein the method is for use with a CT system.

17. The method of claim 3, wherein the electromagnetic radiation comprises at least one of visible light and ultraviolet radiation.

18. The method of claim 2, wherein the additional radiation is an electromagnetic radiation.

19. The method of claim 18, wherein the electromagnetic radiation comprises at least one of visible light and ultraviolet radiation.

20. The method of claim 12, wherein the energy of the additional radiation is no more than 20% greater than the energy difference of the band-to-band transitions.

21. The method of claim 20, wherein the energy of the additional radiation is no more than 15% greater than the energy difference of the band-to-band transitions.

22. A CT system, comprising:
- the direct-converting X-ray radiation detector of claim 13.

* * * * *